United States Patent
Lokhandwalla et al.

(10) Patent No.: US 7,822,457 B2
(45) Date of Patent: Oct. 26, 2010

(54) COMPRESSION PADDLE MEMBRANE AND TENSIONING APPARATUS FOR COMPRESSING TISSUE FOR MEDICAL IMAGING PURPOSES

(75) Inventors: Murtuza Lokhandwalla, Clifton Park, NY (US); Ajay Kapur, Clifton Park, NY (US); Donald Joseph Buckley, Jr., Schenectady, NY (US)

(73) Assignee: General Electric Company, Hiskayuna, NY (US)

( * ) Notice: Subject to any disclaimer, the term of this patent is extended or adjusted under 35 U.S.C. 154(b) by 794 days.

(21) Appl. No.: 10/723,318

(22) Filed: Nov. 25, 2003

(65) Prior Publication Data

US 2005/0113683 A1 May 26, 2005

(51) Int. Cl.
*A61B 5/05* (2006.01)
*A61B 6/04* (2006.01)

(52) U.S. Cl. ........................................ 600/407; 378/37
(58) Field of Classification Search ................ 600/427, 600/437, 415; 378/37, 62, 63, 77; 382/128; 128/915, 109.1, 118.1, 845, 99.1; 602/13
See application file for complete search history.

(56) References Cited

U.S. PATENT DOCUMENTS

| | | | | |
|---|---|---|---|---|
| 3,971,950 A | | 7/1976 | Evans et al. .................. 250/451 |
| 4,620,382 A | * | 11/1986 | Sallis .......................... 38/102.2 |
| 4,691,333 A | | 9/1987 | Gabriele et al. ................ 378/37 |
| 4,885,827 A | * | 12/1989 | Williams ...................... 29/91.1 |
| 5,553,111 A | | 9/1996 | Moore et al. ................... 378/37 |
| 6,128,523 A | * | 10/2000 | Bechtold et al. ............ 600/411 |
| 6,243,484 B1 | * | 6/2001 | Godik .......................... 382/128 |
| 6,574,499 B1 | | 6/2003 | Dines et al. .................. 600/427 |
| 6,682,484 B1 | * | 1/2004 | Entrekin et al. ............. 600/437 |
| 6,850,590 B2 | * | 2/2005 | Galkin .......................... 378/37 |
| 2002/0004630 A1 | * | 1/2002 | Sarvazyan et al. ........... 600/372 |
| 2002/0032373 A1 | * | 3/2002 | Godik et al. ................. 600/300 |
| 2003/0167004 A1 | | 9/2003 | Dines et al. |
| 2004/0010193 A1 | * | 1/2004 | Entrekin et al. ............. 600/437 |
| 2004/0090334 A1 | * | 5/2004 | Zhang et al. ................. 340/575 |

FOREIGN PATENT DOCUMENTS

DE 19610802 9/1997
DE 19901724 7/2000

* cited by examiner

*Primary Examiner*—Long V Le
*Assistant Examiner*—Jacqueline Cheng
(74) *Attorney, Agent, or Firm*—Jenifer E. Haeckl

(57) ABSTRACT

Apparatus for compressing tissue to be scanned for medical imaging is provided. The apparatus may comprise a compression membrane and a tensioning apparatus coupled to the membrane to apply a tensile force to the membrane to place the membrane in a taut condition during an imaging process. In one exemplary application that combines ultrasound scanning with X-ray mammography, the compressing apparatus enables accurate, reproducible ultrasound images reducing distortion and attenuation, which may otherwise be introduced as a consequence of such a combination of imaging processes.

13 Claims, 2 Drawing Sheets

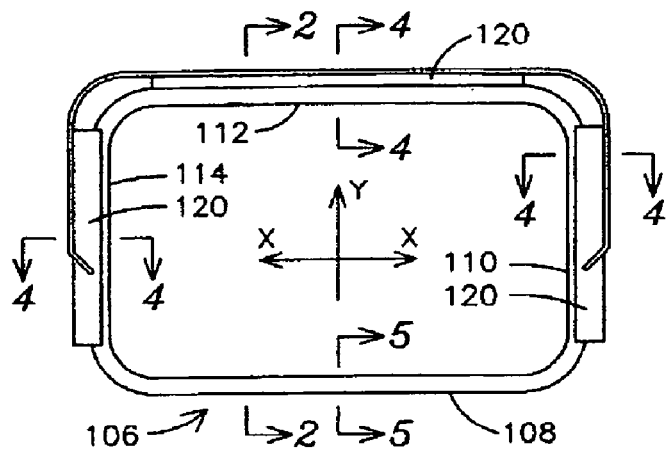
FIG. 3
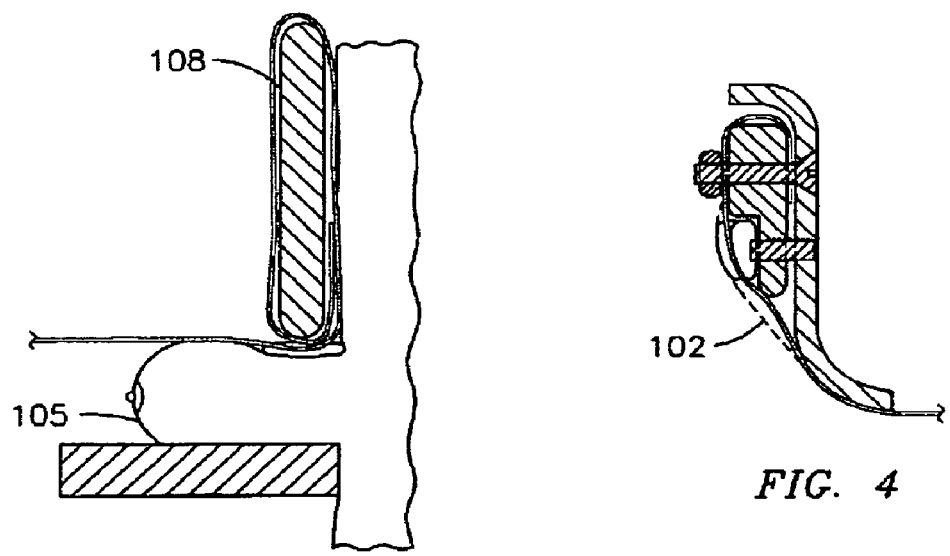
FIG. 5
FIG. 4
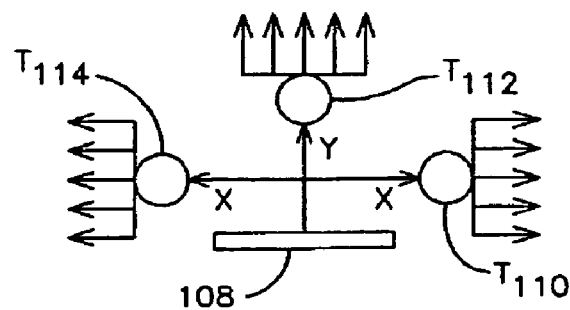
FIG. 7

COMPRESSION PADDLE MEMBRANE AND TENSIONING APPARATUS FOR COMPRESSING TISSUE FOR MEDICAL IMAGING PURPOSES

This invention was made with U.S. Government support through Government Contract Number RO1-CA-91713-01A1 awarded by the National Institute of Health, and, in accordance with the terms set forth in said contract, the U.S. Government may have certain rights in the invention.

BACKGROUND OF THE INVENTION

The present invention is generally related to a probe interface assembly, and, more particularly, to a compliant probe interface assembly for imaging breast tissue with an ultrasound probe in conjunction with X-ray mammography, thereby providing geometrically registered X-ray and ultrasound images.

FIG. 1 illustrates a schematic of conventional X-ray mammographic equipment combined with an ultrasound scanning system. This usually includes a compression plate 10 (e.g., a plate made up of polycarbonate such as Lexan or other suitable materials) to compress and flatten breast tissue 12 against a detector plate 18. In order to perform an ultrasound scan subsequent to an X-ray mammogram, the system further includes an ultrasound probe 14, as may be positioned to traverse atop such a plate to generate ultrasonic images of the internal structure of the breast tissue. A gel 16 may be provided as shown in FIG. 1. The gel typically comprises a suitable composition for reducing acoustic impedance mismatch and reflectance at the plate/probe interface. Ideally, the compression action should provide uniform contact of the breast tissue with the compression plate to achieve appropriate ultrasound propagation as well as superior X-ray imaging.

In practice, the compressing surface of the compression plate may deform when exposed to typical mammographic breast compression forces. The resulting maximum deflection of the plate, as may be measured from a horizontal plane, should be typically constrained to lie within 1 cm, as per MQSA requirements. Since the ultrasound probe 14 rides on top of this deformed plate, as shown in FIG. 1, the ultrasonic beam propagates through a non-uniform gap and a non-parallel surface.

A varying gap changes the ultrasound path between the probe and the compression plate and leads to inconsistent attenuation. A non-parallel surface may lead to variable beam refraction, as the ultrasound beam may be formed from multiple elements in a linear array ultrasound probe. Each of these conditions could have adverse effects on the ultrasound image quality. These conditions may also make it burdensome for a radiologist to correlate an X-ray image to an ultrasound image due to the lack of a consistently reproducible setup from one scan to the next scan.

A thicker plastic plate or a metallic plate would reduce the deflections but would have detrimental effects on ultrasound and x-ray image quality. A relatively thin compression member would reduce ultrasound attenuation. However, a thinner compression member by itself is not a viable solution since a thinner member would have excessive deformation resulting in a non-planar scan surface for the ultrasound probe. In one known compression member, use of a 1 mil (0.025 mm) thick Kapton plate typically results in deformations far exceeding 1 cm when subjected to maximum compression loads of 20 dekanewtons (dkN). Also a non-planar surface, resulting from the usage of a thin membrane, is not easily amenable to automated ultrasound scan. Image reconstruction also becomes complicated and would require processing additional information such as probe orientation relative to scan surface.

BRIEF SUMMARY OF THE INVENTION

Generally, the present invention fulfills the foregoing needs by providing, in one aspect thereof, apparatus for compressing tissue to be scanned for medical imaging. The apparatus comprises a compression membrane and a tensioning apparatus coupled to the membrane to apply a tensile force to the membrane to place the membrane in a taut condition during an imaging process.

In another aspect thereof, the present invention further fulfills the foregoing needs by providing medical imaging equipment comprising apparatus for compressing tissue to be scanned during an imaging process. The apparatus in turn comprising a compression membrane and a tensioning apparatus coupled to the membrane to apply a tensile force to the membrane to place the membrane in a taut condition during an imaging process.

BRIEF DESCRIPTION OF THE DRAWINGS

The features and advantages of the present invention will become apparent from the following detailed description of the invention when read with the accompanying drawings in which:

FIG. 3 is a sectional view along a cutting plane that horizontally traverses the compression paddle membrane and the tensioning apparatus.

FIG. 4 is a sectional view of one of several tensioning devices that may comprise the tensioning apparatus; respective sectional views for such tensioning devices may be taken along respective cutting planes represented by lines 4-4 in FIG. 3.

FIG. 5 is a sectional view at a location where the compression paddle butts against the patient chest wall and as viewed along a cutting plane represented by line 5-5 in FIG. 3.

FIGS. 6 and 7 respectively illustrate exemplary free body diagrams of tensile forces as may be applied to the compression paddle membrane by tensioning devices respectively corresponding to the sectional views depicted in FIGS. 2 and 3.

DETAILED DESCRIPTION OF THE INVENTION

The inventors of the present invention have recognized an innovative means for compressing tissue to be scanned for medical imaging purposes, such as during an automated ultrasound breast scan that may be combined with an X-ray mammogram. Aspects of the present invention enable accurate, reproducible ultrasound images reducing distortion and attenuation, which may be introduced as a consequence of combining the ultrasound scanning with X-ray mammography.

In one exemplary embodiment, a thin polymeric membrane may be used to compress the breast tissue. The membrane thinness (e.g., <0.5 mm) advantageously minimizes ultrasound attenuation (~1 dB). Since the membrane is virtually devoid of any stiffness, a tensioning apparatus 90 is utilized to apply tensile forces that pulls the membrane taut and prevents it from excessive deflection. In one exemplary embodiment, this tensioning apparatus enables the membrane to apply compression loads up to ~30 dkN with deformations comparable and even less than those achieved using a conventional rigid plastic paddle, e.g., 5 mm maximum deflection at the plate center for 20 dkN compression load. The tensile forces may be of the order of 1000N and are borne by a supporting frame structure. The frame structure could be either metallic, polymeric or a composite material suitable for sustaining the tension loads. The functional requirements of this frame are that it should bear the afore-mentioned tensioning load and should not scatter X-ray beams, creating artifacts in the X-ray images. Aspects of the present invention allow effectively balancing several conflicting objectives for obtaining an image quality equivalent to that of a handheld ultrasound while enabling the application of compression loads appropriate for x-ray mammograms. The tensioning could be selectively adjusted by an operator to, for example, relax the deflection criteria for the purpose of providing increased contact of the membrane with the lateral, medial and sub-aerolar regions of the breast.

Figure 1:
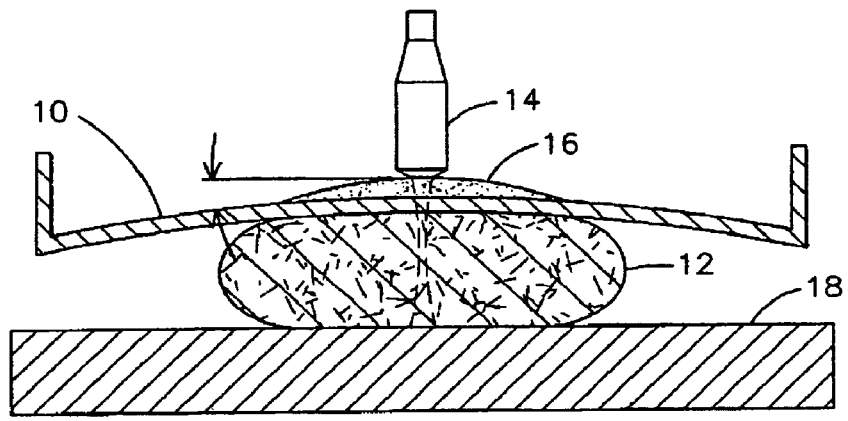
FIG. 1 in part illustrates a sectional view of components of an exemplary automated breast imaging system including a compression plate that may deflect when subjected to compression forces during a scan of breast tissue.
Figure 2:
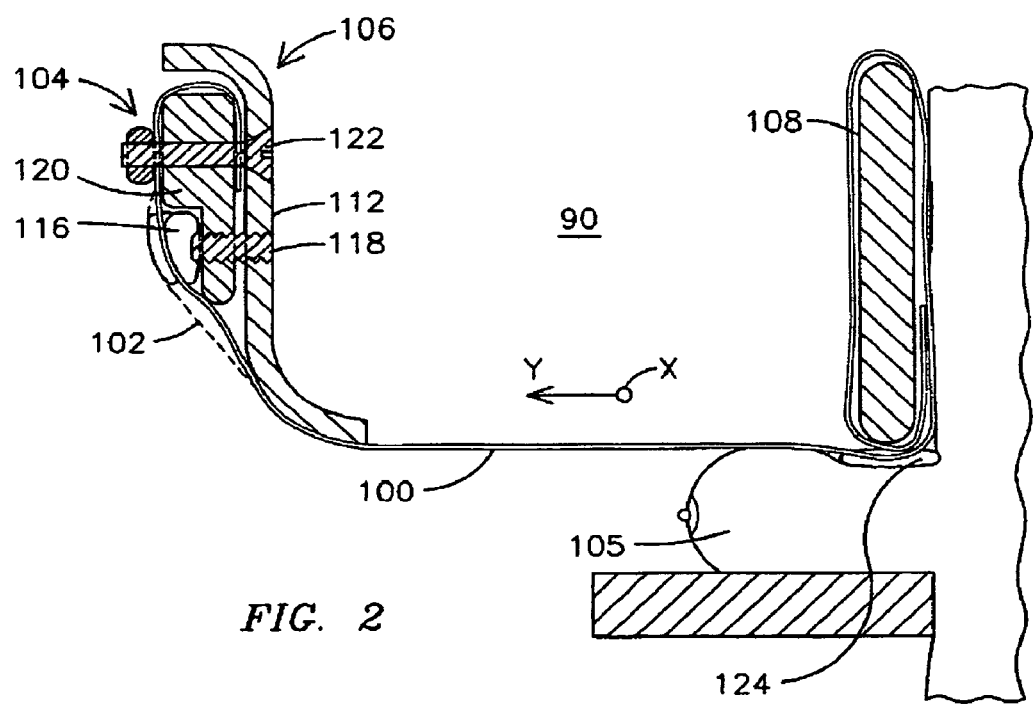
FIG. 2 is a sectional view along a cutting plane represented by line 2-2 in FIG. 3 that vertically traverses an exemplary compression paddle membrane and a tensioning device, part of a tensioning apparatus for such a membrane.

As shown in the sectional view of FIG. 2, a membrane 100 (e.g., a thin polymeric membrane) may be placed in a taut condition, represented by dashed line 102, in response to tensile forces applied with a tensioning device 104 to the membrane 100 in order to compress tissue to be imaged, e.g., breast tissue 105. As explained in further detail below, tensioning device 104 may be part of a tensioning apparatus configured to apply tensile forces to the membrane along a pair of mutually orthogonal co-planar axes so that such a membrane is kept sufficiently taut along the plane defined by such axes. See for example a set of orthogonal axes X, Y in FIGS. 2 and 3. As used herein, a "taut condition" refers to a condition wherein the membrane may apply a compression load ranging from about 5 to about 30 dkN (and, more preferably, from about 10 to about 20 dkN) without experiencing a maximum deflection of 2 cm (and, more preferably, without experiencing a maximum deflection ranging from about 5 to about 10 mm).

A support frame 106 provides support to the membrane 100 and is designed to withstand the applied tension forces. In one exemplary embodiment, membrane 100 may comprise, by way of example, a 0.3 mm thick sheet of polycarbonate or other plastic wrapped around the sides of the support frame.

FIG. 3 illustrates an exemplary embodiment of the support frame 106 comprising a rectangular configuration with frame sides 108, 110, 112 and 114. It will be understood that the present invention is not limited to the exemplary configuration of FIG. 3 since other configurations may be adapted for a given application, e.g., triangular, quadrilateral, oval, etc. It will be further understood by those skilled in the art that any of various materials may be utilized for the membrane 100 provided such materials are sufficiently radiolucent, sonolucent and acoustically matched with the components in the ultrasound beam path, and sufficiently transparent for breast positioning purposes.

In one exemplary embodiment, one end of the membrane 100 may be wrapped around the frame side 108, such as may be positioned parallel to the chest wall of the patient, thus preventing slippage due to tensioning. On the other three sides of the frame, such as frame sides 110, 112, and 114 and as seen in FIG. 3, the membrane is placed in a taut condition by one of several tensioning devices 104 that may collectively make up the tensioning apparatus.

FIG. 2 shows in greater detail an example of one of such tensioning devices of the membrane tensioning apparatus positioned to apply tensile forces to the membrane along axis Y. A tension plate 116 is movable to butt against the membrane 100 causing it to tighten when driven by a setscrew 118, thus enabling to adjust the membrane tension initially, and to subsequently compensate for membrane creep that may develop. It will be now recognized by those skilled in the art that there may be alternative structural means that may work equally effective for applying tension to the membrane 100 in lieu of a tension plate movable by a setscrew. For example, it is contemplated that an inflatable bladder may be responsive to a pressurized fluid, e.g., air, so that when the bladder is fully inflated that bladder would butt against the membrane 100 causing it to tighten. Pressurized fluid would be an example of a hydraulic or pneumatic command for activating the tensioning device. Another example would be a grabbing or pushing device for applying the tensile force to the membrane in lieu of a membrane-pushing device.

A respective clamping plate 120 may be affixed to a corresponding frame side (e.g., each of sides 110, 112 and 114) through a bolt 122 or any other suitable fastening means. Each clamping plate 120 and bolt 122 may be arranged to hold a respective end of the membrane. An adhesive may be optionally used between the membrane ends and the support frame to prevent slipping. As better appreciated in FIG. 2, the chest wall side 108 of the support frame may be rounded in the bottom portion that impinges on the breast and possibly attached to a soft interface material 124, (e.g., gel material) beneath it to reduce patient discomfort. Each of the tensioning devices positioned at the various sides of the support frame (as represented by the sectional view shown in FIG. 4, and taken along the cutting planes represented by lines 4-4 in FIG. 3) may be set to apply different tensile forces to, for example, allow the membrane to deflect differentially across the full frame to ensure better contact with the breast tissues in the rounded regions.

FIG. 5 is a sectional view along a cutting plane represented by line 5-5 in FIG. 3 and is provided to assist the reader to better visualize the relative positioning of various components of a compression paddle membrane and tensioning apparatus embodying aspects of the present invention.

Figure 6:
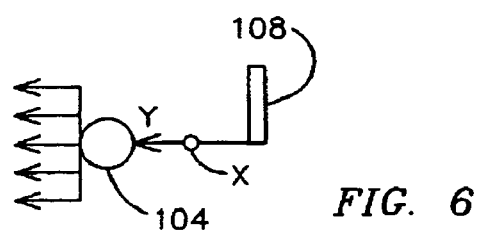

FIG. 6 shows an exemplary free body diagram of tensile forces as may be applied to the compression paddle membrane 100 by a generic tensioning device 104 positioned on frame side 112, as shown in FIG. 2. A generic tensioning device refers to any of the various exemplary tensioning devices and/or techniques discussed above for applying a tensile force to the membrane.

FIG. 7 illustrates an exemplary free body diagram of tensile forces as may be applied to the compression paddle membrane by tensioning devices corresponding to the respective sectional views depicted in FIG. 3. For example, the nodes labeled $T_{114}$ and $T_{110}$ represent generic tensioning devices positioned on opposite sides 114 and 110 to apply tensile forces along the X axis. The node labeled $T_{112}$ represents the tensioning device positioned on side 112 to apply tensile forces along the Y axis.

While the preferred embodiments of the present invention have been shown and described herein, it will be obvious that such embodiments are provided by way of example only. Numerous variations, changes and substitutions will occur to those of skill in the art without departing from the invention herein. Accordingly, it is intended that the invention be limited only by the spirit and scope of the appended claims.

What is claimed is:

1. Apparatus for compressing tissue on a support during a medical imaging process to generate a medical image, said apparatus comprising:
    a tissue compression membrane configured to compress the tissue between the membrane and the support during the medical imaging process and configured to minimize image distortion in the medical image;
    a support frame configured to support at least one end of said compression membrane; and
    a plurality of tensioning apparatuses coupled to said membrane to apply a tensile force to said membrane to place said membrane in a taut condition during the medical imaging process;
    wherein said tensioning apparatuses each comprises an inflatable bladder.

2. The apparatus of claim 1 wherein said support frame further supports said tensioning apparatus.

3. The apparatus of claim 1 wherein said tensioning apparatus comprises at least one tensioning device situated on one side of the frame, and configured to apply tensile force along an axis perpendicular to said frame side.

4. The apparatus of claim 3 wherein said inflatable bladder is at least in part responsive to one of the following commands for applying the tensile force: a hydraulic command and a pneumatic command.

5. The apparatus of claim 1 wherein said compression membrane has a thickness not exceeding 0.5 mm.

6. The apparatus of claim 1 wherein said compression membrane comprises a polymeric material.

7. The apparatus of claim 1 wherein said tissue comprises breast tissue and said imaging process is selected from the group consisting of ultrasound and X-ray mammography.

8. The apparatus of claim 1 wherein said tensioning apparatus comprises means for applying a respective tensile force to said compression membrane along a pair of mutually orthogonal axes that define a plane at least over a portion of said compression membrane.

9. Apparatus for compressing tissue on a support during a medical imaging process to generate a medical image, the apparatus comprising:
    a tissue compression membrane configured to compress the tissue between the membrane and the support during the medical imaging process and configured to minimize image distortion in the medical image;
    a support frame configured to support at least one end of said compression membrane; and
    a plurality of tensioning apparatuses coupled to the membrane to apply a tensile force to the membrane to place the membrane in a taut condition during the medical imaging process;
    wherein the tensioning apparatuses each comprises an inflatable bladder configured to apply a respective tensile force to the compression membrane along a pair of mutually orthogonal axes that define a plane at least over a portion of the compression membrane; and
    wherein applying the tensile force along the orthogonal axes includes means for independently adjusting the magnitude of the tensile force along each of the orthogonal axes, thus allowing to compensate for variation in size and/or shape of the tissue to be compressed.

10. A method for compressing tissue to be scanned for medical imaging to generate a medical image, said method comprising:
    providing a tissue compression membrane that minimizes image distortion in the medical image;
    providing a plurality of inflatable bladders; and
    applying a tensile force to said membrane to place said membrane in a taut condition during an imaging process;
    wherein said tensile force is applied at least in part by said inflatable bladders, and wherein said inflatable bladders can be individually adjusted to selectively apply differing tensile forces to said compression membrane in two or more directions.

11. The method of claim 10 wherein said applying of the tensile force to the compression membrane comprises applying a respective tensile force to said compression membrane along a pair of mutually orthogonal axes that define a plane at least over a portion of said compression membrane.

12. The method of claim 11 wherein the applying of a respective tensile force along said orthogonal axes further comprises independently adjusting the magnitude of the tensile force along each of said orthogonal axes, thus allowing to compensate for variation in size and/or shape of the tissue to be compressed.

13. Medical imaging equipment for imaging tissue comprising:
    apparatus for compressing the tissue during a medical imaging process to generate a medical image, the apparatus comprising:
        a tissue compression membrane configured to minimize image distortion in the medical image;
        a support frame configured to support at least one end of said compression membrane; and
        a plurality of tensioning apparatuses coupled to the membrane to apply a tensile force to the membrane to place the membrane in a taut condition during an imaging process;
        wherein each of the tensioning apparatus comprises an inflatable bladder responsive to one of the following commands for applying the tensile force: a hydraulic command and a pneumatic command;
        wherein at least one of the tensioning apparatus comprises at least two tensioning devices arranged on the support frame to apply a respective tensile force to the compression membrane along a pair of mutually orthogonal axes; and
        wherein each of the tensioning devices includes a respective tension adjuster for independently adjusting the magnitude of the tensile force along each of the orthogonal axes, thus allowing to compensate for variation in size and/or shape of the tissue to be compressed.

* * * * *